US006866039B1

(12) United States Patent
Wright et al.

(10) Patent No.: US 6,866,039 B1
(45) Date of Patent: Mar. 15, 2005

(54) DISPENSING APPARATUS

(75) Inventors: Andrew David Wright, King's Lynn (GB); Hilde Rachel Maria Pollet, Cambridge (GB); Richard Iain Harrison, Buckinghamshire (GB)

(73) Assignee: Bespak PLC (GB)

( * ) Notice: Subject to any disclaimer, the term of this patent is extended or adjusted under 35 U.S.C. 154(b) by 21 days.

(21) Appl. No.: 10/399,167

(22) PCT Filed: Sep. 12, 2001

(86) PCT No.: PCT/GB01/04083

§ 371 (c)(1),
(2), (4) Date: Jul. 29, 2003

(87) PCT Pub. No.: WO02/30500

PCT Pub. Date: Apr. 18, 2002

(30) Foreign Application Priority Data

Oct. 12, 2000 (GB) .......................................... 0025027

(51) Int. Cl.$^7$ ............................................ A61M 13/00
(52) U.S. Cl. ............... 128/203.15; 604/216; 222/321.6; 222/209
(58) Field of Search ............................... 222/83, 321.6, 222/209; 128/203.15; 604/216, 212, 200

(56) References Cited

U.S. PATENT DOCUMENTS

| | | | |
|---|---|---|---|
| 2,307,986 A | | 1/1943 | Bolte et al. |
| 2,672,144 A | | 3/1954 | Cohen |
| 3,272,442 A | | 9/1966 | Rink et al. |
| 3,921,637 A | * | 11/1975 | Bennie et al. ......... 128/203.15 |
| 4,017,007 A | | 4/1977 | Riccio |
| 4,034,899 A | | 7/1977 | Meshberg |
| 4,252,848 A | | 2/1981 | Datta et al. |
| 4,411,656 A | * | 10/1983 | Cornett, III ................. 604/212 |
| 4,417,890 A | | 11/1983 | Dennehey et al. |
| 4,645,487 A | | 2/1987 | Shishov et al. |

(List continued on next page.)

FOREIGN PATENT DOCUMENTS

| | | |
|---|---|---|
| DE | 197 00 838 A1 | 7/1998 |
| DE | 199 42 791 A | 3/2001 |
| EP | 0 360 463 | 3/1990 |
| EP | 0 407 276 A | 1/1991 |
| EP | 0407276 A | 1/1991 |

(List continued on next page.)

*Primary Examiner*—Philippe Derakshani
(74) *Attorney, Agent, or Firm*—Morris, Manning & Martin LLP

(57) ABSTRACT

The present invention relates to a disposable dispensing apparatus for delivering a powdered product nasally or orally. The apparatus comprises a housing (1) defining an outlet (7) and a shaft (32) having a storage chamber (33) therein for a product provided with a first inlet (34) and a first outlet (35). A sheathing means (4) is slidably mounted on the shaft and has a second inlet (42) and a second outlet closed by a frangible membrane (44). There is also provided a variable volume means (2) operatively connected to the shaft. The shaft is movable, on operation of the variable volume means to reduce the variable volume so as to pressurize gas in an interior of the variable volume means, from an initial storage position in which the first and second inlets are out of alignment so as to close a gas flow path, to a dispensing position in which the first and second inlets are brought into alignment by action of the housing against the sheathing means. At the same time, the frangible membrane is ruptured by the shaft so as to open the gas flow path, such that pressurized gas from the interior of the variable volume means is discharged along the gas flow path comprising the first and second inlets, storage chamber, second outlet and first outlet, to thereby entrain powdered product and dispense it through the housing outlet.

35 Claims, 5 Drawing Sheets

U.S. PATENT DOCUMENTS

| | | |
|---|---|---|
| 4,844,986 A | 7/1989 | Karakelle et al. |
| 4,857,080 A | 8/1989 | Baker et al. |
| 4,875,605 A | 10/1989 | Weston |
| 4,948,628 A | 8/1990 | Montgomery et al. |
| 4,966,312 A * | 10/1990 | Waring ............ 604/216 |
| 5,341,800 A | 8/1994 | Clark et al. |
| 5,349,944 A | 9/1994 | Chippendale et al. |
| 5,351,683 A * | 10/1994 | Chiesi et al. ......... 128/203.15 |
| 5,474,758 A | 12/1995 | Kwon |
| 5,490,497 A | 2/1996 | Chippendale et al. |
| 5,576,068 A | 11/1996 | Caburet et al. |
| 5,683,361 A * | 11/1997 | Elk et al. ............ 604/200 |
| 5,702,362 A * | 12/1997 | Herold et al. ......... 128/203.15 |
| 5,775,321 A | 7/1998 | Alband |
| 5,836,299 A | 11/1998 | Kwon |
| 5,857,456 A | 1/1999 | Sun et al. |
| 5,871,010 A | 2/1999 | Datta et al. |
| 5,884,820 A | 3/1999 | Thanisch et al. |
| 5,904,274 A | 5/1999 | Warby et al. |
| 6,006,745 A | 12/1999 | Marecki |
| 6,039,042 A | 3/2000 | Sladek |
| 6,120,481 A | 9/2000 | Rennert et al. |
| 6,131,566 A | 10/2000 | Ashurst et al. |
| 6,253,762 B1 | 7/2001 | Britto |
| 6,358,569 B1 | 3/2002 | Badyal et al. |
| 6,488,648 B1 * | 12/2002 | Matsugi et al. ....... 128/203.15 |
| 6,782,887 B2 * | 8/2004 | Sullivan ............ 128/203.15 |

FOREIGN PATENT DOCUMENTS

| | | |
|---|---|---|
| EP | 0469926 | 2/1992 |
| EP | 0 808 635 A2 | 11/1997 |
| EP | 0 906 765 A1 | 4/1999 |
| FR | 2 775 963 A | 9/1999 |
| GB | 1 338 254 | 11/1973 |
| GB | 2087355 A | 5/1982 |
| GB | 2 367 756 A | 4/2002 |
| WO | WO 9102558 | 3/1991 |
| WO | WO 9106333 | 5/1991 |
| WO | WO 92/06727 | 4/1992 |
| WO | WO 92 06727 A | 4/1992 |
| WO | WO 93/11818 A | 6/1993 |
| WO | WO 96 28367 A | 9/1996 |
| WO | WO 9632345 | 10/1996 |
| WO | WO 97 32672 | 9/1997 |
| WO | WO 97 47347 | 12/1997 |
| WO | WO 98/51360 | 11/1998 |
| WO | WO 98/55168 | 12/1998 |
| WO | WO 99/42154 | 8/1999 |
| WO | WO 99 42154 | 9/1999 |
| WO | WO 99/46055 | 9/1999 |
| WO | WO 99 46055 A | 9/1999 |
| WO | WO 99 49923 A | 10/1999 |
| WO | WO 00/16835 | 3/2000 |
| WO | WO 2001/010742 A1 | 2/2001 |
| WO | WO 01 43529 A | 6/2001 |
| WO | WO 02 305500 A | 4/2002 |

* cited by examiner

DISPENSING APPARATUS

The present application is the national stage of international patent application PCT/GB01/04083, filed Sep. 12, 2001, which is incorporated herein by reference, and which claims priority under 35 U.S.C. § 119(a)–(d) to GB 0025027.4.

The present invention relates to a disposable dispensing apparatus for delivering a powdered product nasally or orally. In particular there is provided a single-use dry powder medicament inhaler for nasal use.

Single-use dry powder inhalers are known in the art. One such example is shown in U.S. Pat. No. 5,683,361. However, the efficiency of delivery of the powdered product in this device is adversely affected due to the upper frangible membrane partially blocking the flow path after it has been ruptured. In other respects there is a need to reduce the manufacturing and assembly costs of single-dose dispensing apparatus.

The present invention provides a dispensing apparatus for dispensing a powdered product comprising: a housing defining an outlet, a shaft having a storage chamber therein for a powdered product provided with a first inlet and a first outlet, sheathing means slidably mounted on the shaft and having a second inlet and a second outlet closed by a frangible membrane, and variable volume means operatively connected to the shaft; wherein the shaft is moveable, on operation of the variable volume means to reduce the variable volume so as to pressurise gas in an interior of the variable volume means, from an initial storage position in which the first and second inlets are out of alignment so as to close a gas flow path, to a dispensing position, in which the first and second inlets are brought into alignment by action of the housing against the sheathing means and in which the frangible membrane is ruptured by the shaft so as to open the gas flow path, such that pressurised gas from the interior of the variable volume means is discharged along the gas flow path comprising the first and second inlets, storage chamber, second outlet and first outlet, to thereby entrain powdered product and dispense it through the housing outlet.

Embodiments of the present invention will now be described, by way of example only, with reference to the accompanying drawings, in which.

Figure 1:
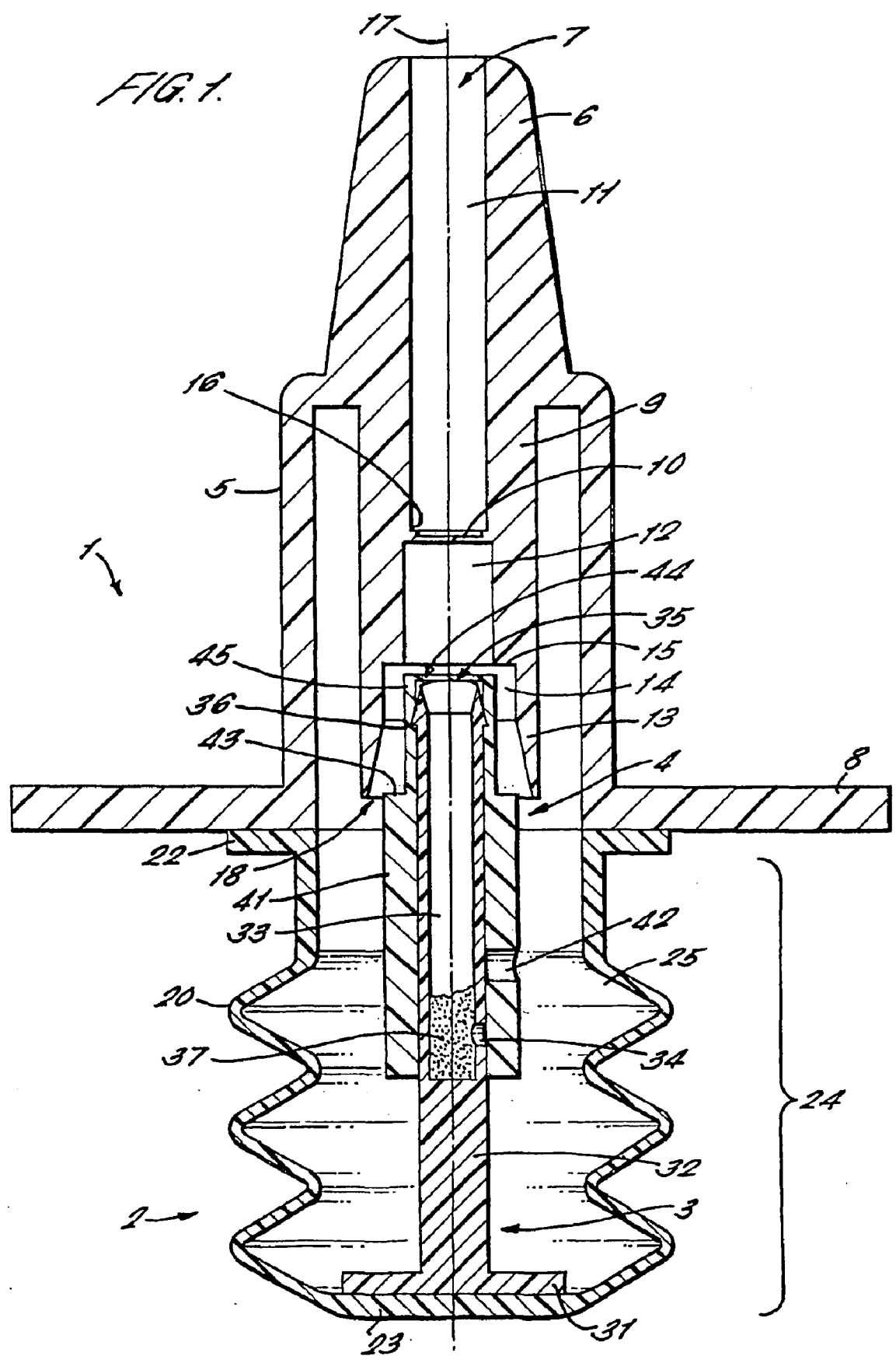
FIG. 1 is a cross-sectional view of a first embodiment of dispensing apparatus according to the present invention in a 'storage' condition.
Figure 2:
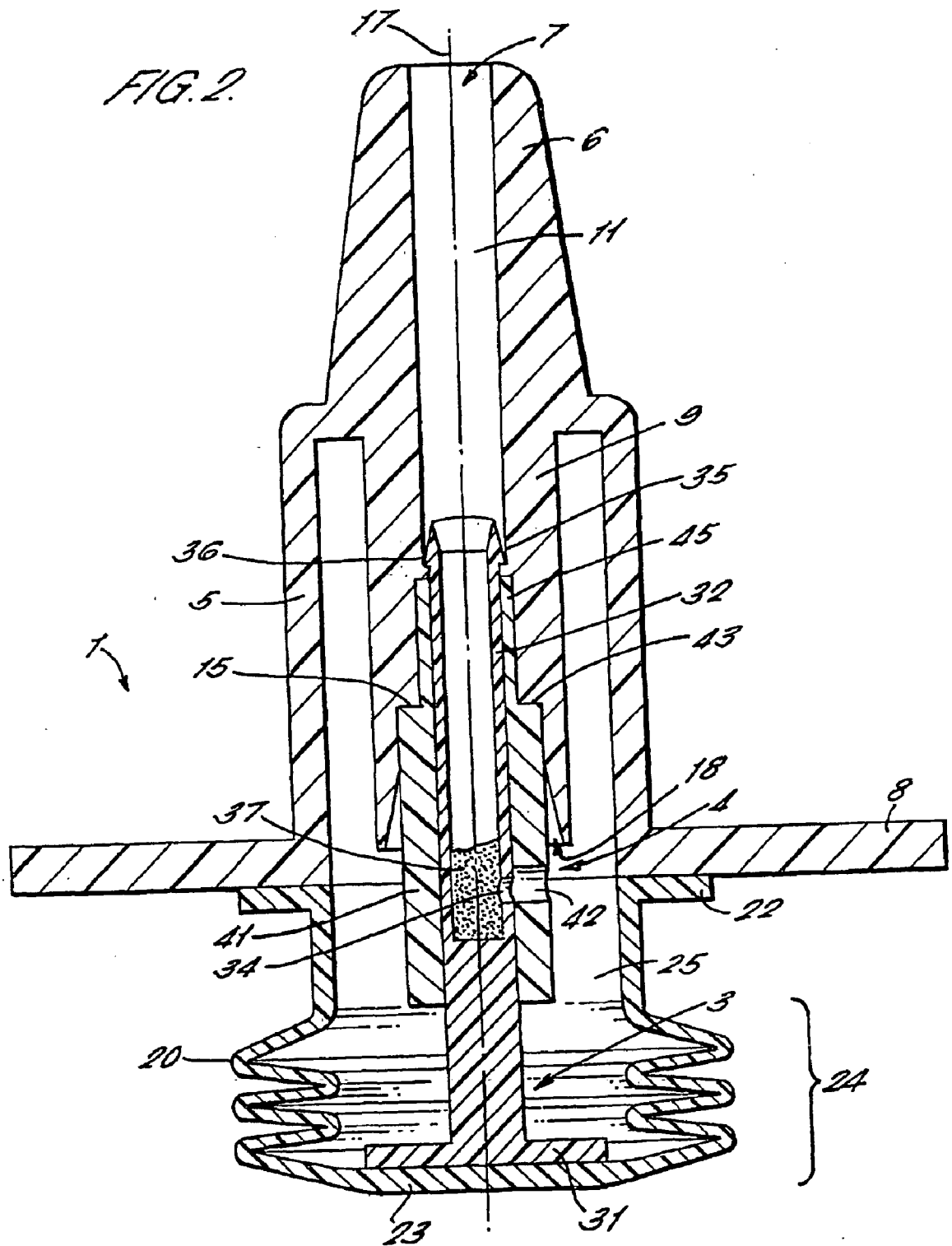
FIG. 2 is a cross-sectional view of the apparatus of FIG. 1 in a 'dispensing' condition.

As shown in FIGS. 1 and 2, a first embodiment of the present invention comprises a housing 1 having a generally cylindrical section 5, tip 6 and finger rests 8. The cylindrical section 5 of the housing 1 is provided with an internal, axially orientated, tubular extension 9. A bore of the tubular extension 9 is closed off part-way along its length by a first frangible membrane 10. The bore defines a duct 12 extending from the first frangible membrane 10 in a direction of an open end 18 of the tubular extension 9 and an outlet duct 11 extending from the first frangible membrane 10 in a direction of the tip 6. The extremity of the outlet duct 11 distal the first frangible membrane 10 defines an outlet 7 in tip 6. Preferably the duct 12 and outlet duct 11 both extend along a longitudinal axis 17 of the housing 1.

The open end 18 of duct 12 is provided with a frusto-conically shaped mouth 13 leading to a bore portion 14 of enlarged diameter. The junction between the duct 12 and bore portion of enlarged diameter 14 defines an annular internal shoulder 15.

The finger rests 8 may be formed by a single annular flange extending from the cylindrical section or by two or more separate flanges circumferentially spaced around the cylindrical section 5.

A bellows unit 2 is joined to the housing 1. The bellows unit 2 comprises an annular mounting flange 22 and an axially extending bellows portion 24 having a plurality of concertina formations 20 formed therein. An end of the bellows unit 2 distal the mounting flange 22 is closed off by an end face 23 defining a finger or thumb rest.

A probe 3 is provided within the bellows unit 2 and housing 1. The probe 3 comprises a cylindrical extension 32 which is mounted by means of a basal flange 31 to the inside of end face 23 so as to lie extending substantially along longitudinal axis 17. The cylindrical extension 32 comprises a hollow portion at an end distal the basal flange 31 defining a powder storage chamber 33. The distal end of the cylindrical extension 32 is shaped to form a piercing tip 35 and is provided with retaining barbs 36. A radially directed aperture 34 is provided in the wall of the cylindrical extension 32 communicating with the storage chamber 33.

A sheath 4 is slidably mounted on the cylindrical extension 32. The sheath 4 comprises a cylindrical portion 41 having a radially orientated aperture 42 therein and a reduced diameter portion 45 being closed at one end by a second frangible membrane 44. The junction between the cylindrical portion 41 and reduced diameter portion 45 defines an external annular shoulder 43. The internal diameter of the sheath 4 is such that sliding movement between the sheath 4 and probe 3 is facilitated while maintaining a air-tight seal therebetween. Optionally sliding seal members, such as O-rings, may be provided between the sheath 4 and probe 3 to improve the seal integrity.

The powdered product to be dispensed is held in the storage chamber 33.

In a storage position, as shown in FIG. 1, the sheath 4 is mounted on probe 3 with the piercing tip 35 in close proximity to or abutting against the second frangible membrane 44. In this position the radial apertures 34 and 42 are out of alignment and there is consequently no open path between an interior 25 of the bellows portion 24 and the storage chamber 33. Thus, the apertures 34 and 42, which together form an inlet valve, are in a 'closed' position.

The housing 1, probe 3 and sheath 4 are manufactured from polyethylene or polypropylene or similar material. Similarly, the frangible membranes 10, 44 are manufactured from polyethylene or polypropylene or similar material. Alternatively, the probe 3 may be manufactured from a metal such as stainless steel.

The bellows unit 2 is manufactured from polyethylene, polypropylene, a thermoplastic elastomer or other similarly flexible polymer. The unit 2 may be formed from as a single moulding of a single material. Alternatively, the unit 2 may be formed as a two-part moulding, each part being of a different material.

Advantageously, the materials of the dispensing apparatus lend themselves to easy and ready recycling. In the preferred arrangement, the absence of any metallic or ceramic components reduces the cost of processing the recycled material.

Figure 5A:
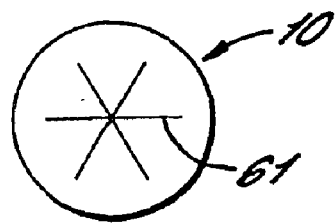
FIGS. 5a and 5b show plan views of two variants of frangible membranes for use in the dispensing apparatus of the present invention.
Figure 5B:
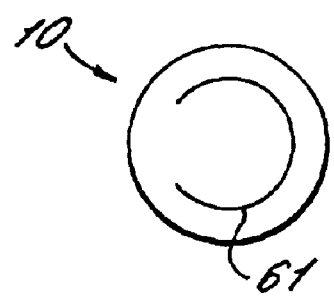

Typically, the thickness of the frangible membranes 10, 44 is between 0.05 and 0.30 mm. As shown in FIGS. 5a and 5b, the first frangible membrane 10 may optionally be provided with one or more pre-formed lines of weakness to aid the rupturing of the membrane by the piercing tip 35. FIG. 5a depicts a 'star' pattern of weaknesses and FIG. 5b depicts a 'half-moon' pattern of weaknesses. In the same way the second frangible membrane 44 may be provided with lines of weakness.

Advantageously, the components of the dispensing apparatus are moulded. This leads to low levels of material waste. The current design allows for a low number of individual parts which reduces assembly time and cost. For example, the whole apparatus may be formed from only three components, the first component being the housing 1 including the first frangible membrane 10, the second component being the bellows unit 22 and probe 3 formed as a unitary part, and the third component being the sheath 4 including the second frangible membrane 44.

In use, a user holds the apparatus typically by means of two or more fingers positioned on the finger rests 8 and a thumb positioned on end face 23. The tip 6 is then inserted into the nose (or mouth if the apparatus is for pulmonary use). Inhalation at this stage is ineffective since the first frangible membrane 10 seals off the outlet duct 11.

The user depresses the end face 23 of the bellows unit 2 so as to move the probe 3 and sheath 4 axially into housing 1 in the direction of tip 6. Initially, the probe 3 and sheath 4 are free to move unhindered with the reduced diameter portion 45 of the sheath 4 being slidingly received in the duct 12. Further movement of the probe 3 and sheath 4 brings the external shoulder 43 of the sheath 4 into contact with the internal shoulder 15 of the tubular extension 9. At this point, further inward movement of the sheath 4 relative to the tubular extension 9 is prevented. Continued inward movement of the probe 3 causes the piercing tip 35 of the probe 3 to pierce and break the second frangible membrane 44. Subsequent inward movement of the probe 3 then causes the piercing tip 35 to pierce and break the first frangible membrane 10 opening communication between the duct 12 and outlet duct 11. Advantageously, both of the frangible membranes 44, 10 are ruptured from below with the piercing means 35 moving relative to the membranes in the direction of tip 6. As a result the 'flap' of the membrane which is left after rupture is positioned above the membrane periphery such that as gas passes the membrane the 'flap' tends to be moved away from the hole formed in the membrane so as not to block the flow path unlike where a membrane is ruptured from above.

As the piercing tip 35 passes through the first frangible membrane 10 the barbs 36 or other snap-fit formations are engaged and retained with an annular lip 16 of the first frangible membrane 10, preventing retraction of the probe 3 in the direction of the bellows unit 2. Advantageously, the barbs 36 prevent any attempt at re-use of the dispensing apparatus and also provide a clear visual indication that the apparatus has been used.

The axial length of the reduced diameter portion 45 of the sheath 4 and the duct 12 can be chosen such that the first and second frangible membranes lie in close proximity at the point of rupture ensuring that the user feel a single, positive sensory signal that the storage chamber 33 has been opened.

Simultaneously with the first and second membranes being ruptured, the relative axial movement of the sheath 4 and probe 3 causes the apertures 34 and 42 to come into alignment, opening the inlet valve of the storage chamber 33. The apparatus is now in the 'dispensing' position, as shown in FIG. 2. In the dispensing position the inlet valve is open and the first and second frangible membranes are ruptured. Thus a continuous flow path is established between the interior 25 of the bellows portion 24 and the outlet 7. As a result air, pressurised during inward movement of the bellows unit's concertinas 20, is displaced from the interior 25 of the bellows portion 24, through the inlet valve formed by the apertures 34 and 42 and into the storage chamber 33 where it entrains the powdered product. The air and entrained product is then displaced through piercing tip 35, duct 12 and outlet duct 11 where it finally exits outlet 7. In this way the apparatus actively dispenses the powdered product so that the necessary inhalatory effort required by the user is reduced or even effectively eliminated.

The degree of compression and pressurisation of the air within the bellows unit 2 provides adequate energy to efficiently entrain and dispense the powdered product with little or no inhalatory effort by the user. Advantageously, this means that the apparatus may be used for dispensing products to users who can provide little inhalatory effort such as children or the elderly as well as to users who are unable to provide any inhalatory effort such as those who are unconscious.

Figure 3:
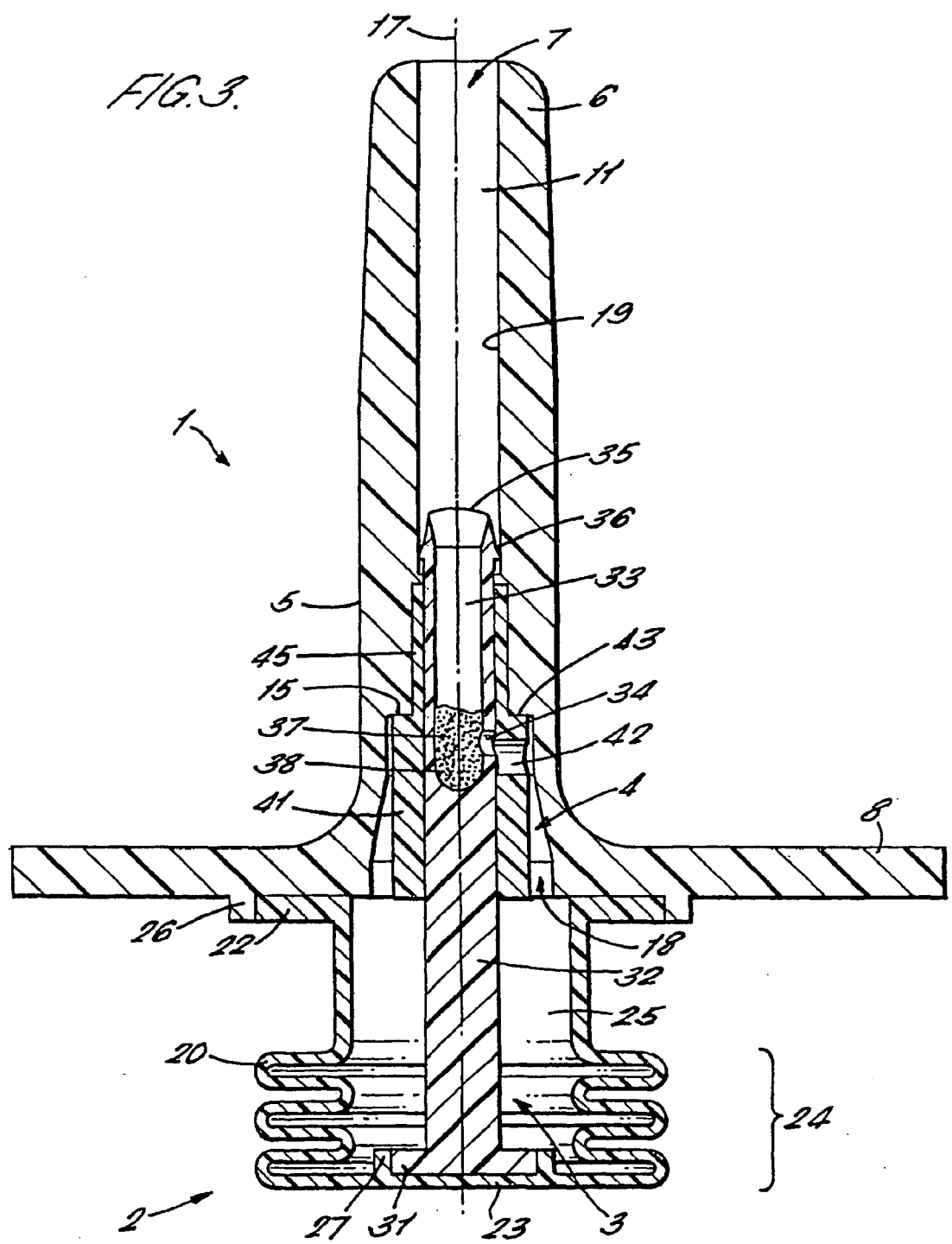
FIG. 3 is a cross-sectional view of a second embodiment of dispensing apparatus according to the present invention in a 'dispensing' condition.

FIG. 3 shows a second embodiment of dispensing apparatus according to the present invention. Similar features to those described above with reference to the first embodiment have been designated with like reference numerals and will not be described in further detail except where they differ in form or function.

The housing 1 of the second embodiment is modified such that the tip 6 and cylindrical section 5 are formed as a single body of substantially constant cross-section. A slight tapering of the tip 6 is preferably provided for the comfort of the user.

The tubular extension 9 is dispensed with. Instead an internal wall 19 of the tip 6 and cylindrical section 5 defines duct 12, outlet duct 11 and internal shoulder 15.

The storage chamber 33 is provided with a hemispherically shaped lower end 38 which is believed to lead to more efficient entrainment and removal of the powdered product from the storage chamber 33. Alternatively the lower end 38 may be V-shaped or U-shaped in cross-section.

The mounting flange 22 is received in an annular socket defined on the finger rests 8 by annular rim 26 leading to a more secure attachment.

Likewise, the basal flange 31 of the probe 3 is received in a socket defined by annular rim 27 formed on the inner surface of end face 23.

The operation of the second embodiment is substantially the same as that of the first embodiment.

The second embodiment has a less complicated form leading to easier moulding of the component parts.

Figure 4:
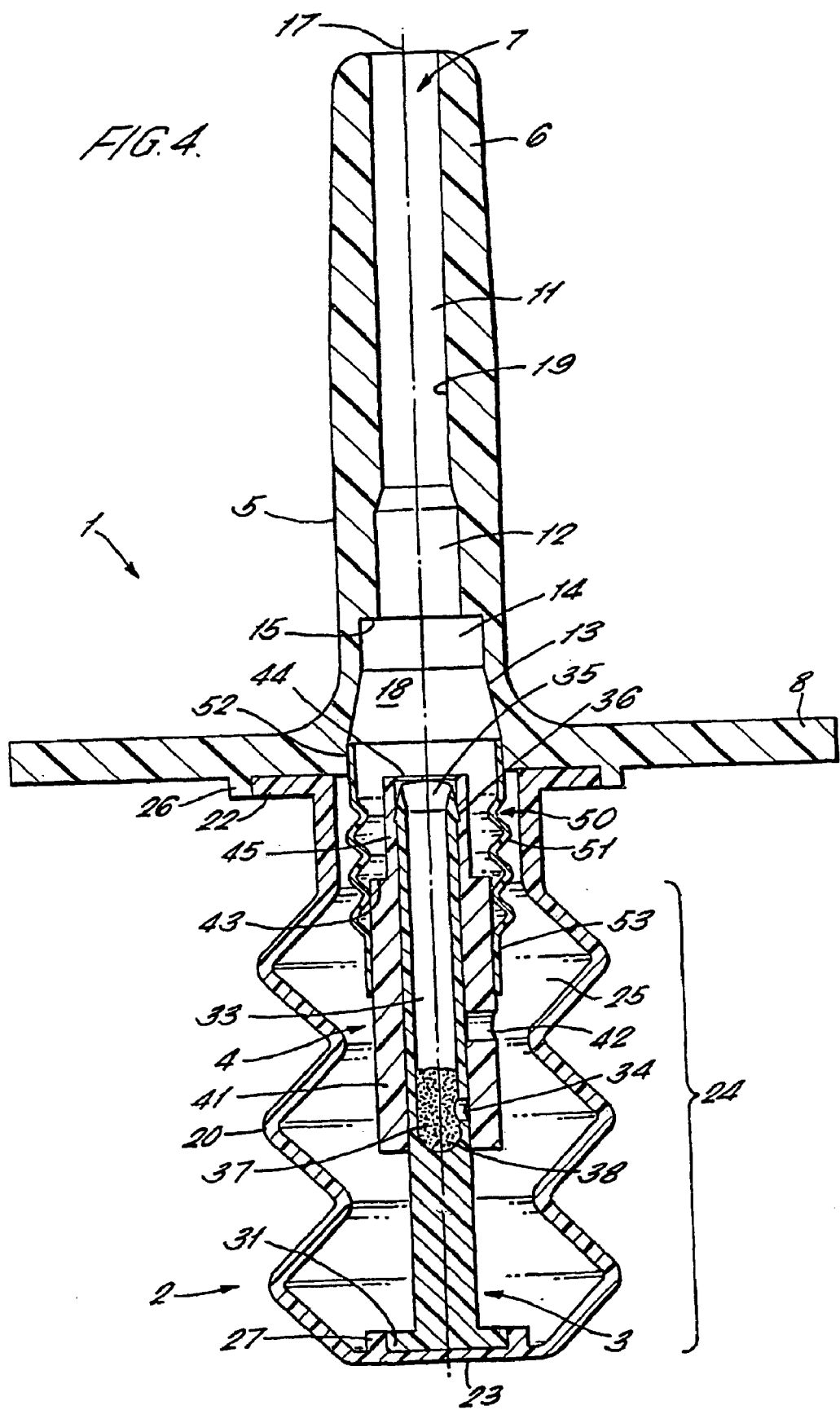
FIG. 4 is a third embodiment of dispensing apparatus according to the present invention in a 'storage' condition.

FIG. 4 shows a third embodiment of dispensing apparatus according to the present invention. Similar features to those described above with reference to the second embodiment have been designated with like reference numerals and will not be described in further detail except where they differ in form or function.

In the third embodiment the first frangible membrane 10 is replaced by a second bellows unit 50. The second bellows unit 50 comprises a bellows section having a number of concertina formations 51, and two sleeve portions 52 and 53.

The first sleeve portion 52 is push-fit into mouth 13 of housing 1. The second sleeve portion 53 is slid as a push-fit over the outer surface of the sheath 4. A snap-fit may be provided between the second sleeve portion 53 and the sheath 4 to aid retention of the sleeve portion on the sheath.

The tip 6 may be profiled so as to more comfortably fit into the nose of the user.

In other ways the third embodiment is similar to the second embodiment.

In use, displacement of the end face 23 by the user cause the probe 3 to be moved inwardly in the direction of tip 6 as with the previous embodiments. Fluid communication between the interior 25 of the bellows portion 24 and the outlet 7 is prevented by the fluid tight seals between the sleeve portions 52, 53 of the second bellows unit 50 and respectively the mouth 13 and sheath 4. The flexibility of the concertina formations 51 of the second bellows unit 50 accommodates the inward movement of the probe 3. Subsequent operation of the apparatus is the same as for the previous embodiments with the piercing tip rupturing the frangible membrane 44.

Figure 6:
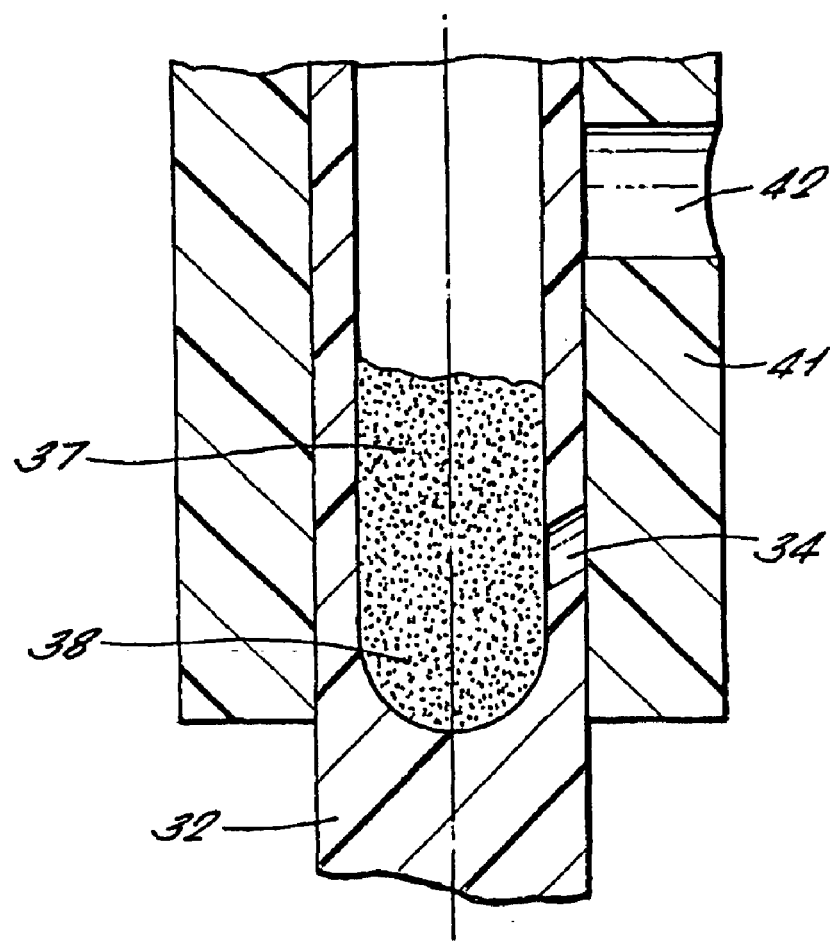
FIG. 6 is a cross-sectional view of a part of the dispensing apparatus of the present invention showing a variant storage chamber inlet aperture.

FIG. 6 shows a variant of the aperture 34 wherein the aperture is directed so as to have a component in the axial direction as well as the radial direction. In this way the air entering the storage chamber 33 is directed towards the closed lower end 38 of the chamber 33 so as to more efficiently entrain the powdered product 37. Alternatively, the inlet aperture 34 may be angled so as to have components in the radial, axial and circumferential directions such that air entering the storage chamber 33 is directed towards the lower end 38 with a 'spiralling' motion. In any of these arrangements the inlet aperture 34 may be positioned so as to be covered or uncovered by the powdered product in the storage condition. More than one aperture 34 may be provided.

Alternatively, the inlet aperture 34 may be positioned in the lower end 38 of the storage chamber 33 such that air entering the chamber enters underneath the powdered product and is directed axially along the chamber 33 towards the piercing tip 35. In a yet further alternative, the powdered product may be suspended on a mesh within the storage chamber 33 such that air entering the storage chamber 33 enters below the mesh and entrains the powdered product as it passes through the mesh.

Optionally, the storage chamber 33 may be provided with rifling grooves or similar along its length to impart a 'spiralling' motion to the air and entrained product as it passes along the chamber towards the piercing tip 35.

The bellows unit 2 may be substituted by a tube with weakened sections, a bulbous sack or a memory returning form.

The finger rests 8 may incorporate a plurality of axially directed flanges aligned co-axially around the bellows unit 2 to form a guard preventing accidental depression of the bellows unit 2.

The dispensing apparatus may be provided in a sterile package such as a foil packet for reasons of hygiene. Alternatively, a cap may be provided to cover and close of outlet 7 before use.

While the apparatus has been specifically described for use as a nasal apparatus, it may equally be used for oral delivery of powdered products. In such a case tip 6 may be advantageously replaced by a mouthpiece.

Features of the invention which have been described in the context of separate embodiments may also be provided in combination in a single embodiment. Conversely, the features of the invention which have been described in a single embodiment may be provided separately or in any suitable sub-combination.

What is claimed is:

1. Dispensing apparatus for dispensing a powdered product comprising:
   a housing defining an outlet,
   a shaft having a storage chamber therein for a powdered product provided with a first inlet and a first outlet,
   a sheathing member slidably mounted on the shaft and having a second inlet and a second outlet closed by a frangible membrane, and
   a variable volume member operatively connected to the shaft;
   wherein the shaft is moveable, on operation of the variable volume member to reduce the variable volume so as to pressurize gas in an interior of the variable volume member, from an initial storage position in which the first and second inlets are out of alignment so as to close a gas flow path, to a dispensing position, in which the first and second inlets are brought into alignment by action of the housing against the sheathing member and in which the frangible membrane is ruptured by the shaft so as to open the gas flow path, such that pressurized gas from the interior of the variable volume member is discharged along the gas flow path comprising the first and second inlets, storage chamber, second outlet and first outlet, to thereby entrain powdered product and dispense it through the housing outlet.

2. Dispensing apparatus as claimed in claim 1 wherein the housing further comprises means for sealing the housing outlet in the storage position.

3. Dispensing apparatus as claimed in claim 1 wherein the housing further comprises a second frangible membrane which is ruptured by the shaft as the shaft moves from the storage position to the dispensing position.

4. Dispensing apparatus as claimed in claim 1 wherein the housing further comprises is a flexible member sealing between the sheathing member and the housing.

5. Dispensing apparatus as claimed in claim 1 wherein the shaft is adapted such that the or each frangible membrane is ruptured by the shaft moving relative to the frangible membrane in the direction of the housing outlet.

6. Dispensing apparatus as claimed in claim 1 wherein the or each frangible membrane comprises one or more pre-formed lines of weakness.

7. Dispensing apparatus as claimed in claim 1 wherein the or each frangible membrane is 0.05 to 0.30 mm thick.

8. Dispensing apparatus as claimed in claim 1 wherein as the shaft moves from the storage position to the dispensing position the sheathing member abuts an inwardly directed shoulder of the housing.

9. Dispensing apparatus as claimed in claim 8 wherein the inwardly directed shoulder is formed within a tubular extension of the housing.

10. Dispensing apparatus as claimed in claim 9 wherein a mouth of the tubular extension which receives the shaft as it moves from the storage position to the dispensing position has a frusto-conical form.

11. Dispensing apparatus as claimed in any of claims 8 to 10 wherein the sheathing member comprises an outwardly directed shoulder which abuts the inwardly directed shoulder of the housing as the shaft moves from the storage position to the dispensing position.

12. Dispensing apparatus as claimed in claim 1 wherein the sheathing member forms a sliding seal against the shaft.

13. Dispensing apparatus as claimed in claim 12 wherein one or more sealing members are provided between the sheathing member and the shaft.

14. Dispensing apparatus as claimed in claim 1 wherein the axis of the first inlet of the shaft is radially directed.

15. Dispensing apparatus as claimed in claim 1 wherein the axis of the first inlet of the shaft is axially directed.

16. Dispensing apparatus as claimed in claim 1 wherein the axis of the first inlet of the shaft is directed to have both radial and axial components.

17. Dispensing apparatus as claimed in claim 1 wherein the axis of the first inlet of the shaft is directed to have radial, axial and circumferential components.

18. Dispensing apparatus as claimed in claim 1 wherein the storage chamber has more than one inlet.

19. Dispensing apparatus as claimed in claim 18 wherein the inlets are displaced axially relative to one another along the length of the storage chamber.

20. Dispensing apparatus as claimed in claim 1 wherein the first inlet of the shaft is located above the level of powdered product stored within the storage chamber.

21. Dispensing apparatus as claimed in claim 1 wherein the first inlet of the shaft is located below the level of powdered product stored within the storage chamber.

22. Dispensing apparatus as claimed in claim 1 wherein the storage chamber in the shaft comprises a hemi-spherical, V-shaped or U-shaped base.

23. Dispensing apparatus as claimed in claim 1 wherein the internal walls of the storage chamber are rifled.

24. Dispensing apparatus as claimed in claim 1 wherein the shaft comprises a piercing member for rupturing the or each frangible membrane.

25. Dispensing apparatus as claimed in claim 1 wherein the shaft comprises means for engaging the housing and retaining the shaft relative to the housing when in the dispensing position.

26. Dispensing apparatus as claimed in claim 1 wherein the shaft comprises one or more reverse-directed projections adjacent the outlet of the shaft for engaging the housing and retaining the shaft relative to the housing when in the dispensing position.

27. Dispensing apparatus as claimed in claim 1 wherein the variable volume member is a bellows.

28. Dispensing apparatus as claimed in claim 1 wherein the variable volume member is a flexible sac.

29. Dispensing apparatus as claimed in claim 1 wherein the variable volume member is a tube with weakened sections.

30. Dispensing apparatus as claimed in claim 1 wherein at least the housing is a moulded component.

31. Dispensing apparatus as claimed in claim 30 wherein the shaft is a moulded component.

32. Dispensing apparatus as claimed in claim 30 wherein the sheathing member is a moulded component.

33. Dispensing apparatus as claimed in claim 1 formed from on or more of polyethylene, polypropylene or other thermoplastic elastomer.

34. Dispensing apparatus as claimed in claim 1 adapted for nasal delivery of powdered products.

35. Dispensing apparatus as claimed in claim 1 adapted for oral delivery of powdered products.

* * * * *